US008801601B2

(12) United States Patent
Prisco et al.

(10) Patent No.: US 8,801,601 B2
(45) Date of Patent: Aug. 12, 2014

(54) METHOD AND SYSTEM FOR PROVIDING VISUAL GUIDANCE TO AN OPERATOR FOR STEERING A TIP OF AN ENDOSCOPIC DEVICE TOWARD ONE OR MORE LANDMARKS IN A PATIENT

(71) Applicants: Giuseppe Maria Prisco, Pontedera (IT); Vincent Duindam, Mountain View, CA (US)

(72) Inventors: Giuseppe Maria Prisco, Pontedera (IT); Vincent Duindam, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/678,917

(22) Filed: Nov. 16, 2012

(65) Prior Publication Data

US 2013/0144124 A1 Jun. 6, 2013

Related U.S. Application Data

(63) Continuation of application No. 12/411,515, filed on Mar. 26, 2009, now Pat. No. 8,337,397.

(51) Int. Cl.
*A61B 1/04* (2006.01)
*A61B 5/05* (2006.01)

(52) U.S. Cl.
USPC ............ 600/117; 600/424; 600/423; 600/426

(58) Field of Classification Search
CPC ................... A61B 19/5244; A61B 2019/5251; A61B 2019/5272
USPC ............. 434/262; 604/528, 529; 606/46, 108; 128/899
See application file for complete search history.

(56) References Cited

U.S. PATENT DOCUMENTS

| | | | | | |
|---|---|---|---|---|---|
| 5,517,990 | A | * | 5/1996 | Kalfas et al. | 600/414 |
| 5,638,819 | A | | 6/1997 | Manwaring et al. | |
| 5,729,129 | A | | 3/1998 | Acker | |
| 5,732,703 | A | * | 3/1998 | Kalfas et al. | 600/407 |
| 5,765,561 | A | | 6/1998 | Chen et al. | |
| 5,776,050 | A | | 7/1998 | Chen et al. | |
| 5,797,849 | A | | 8/1998 | Vesely et al. | |
| 5,928,248 | A | * | 7/1999 | Acker | 623/1.11 |
| 5,951,475 | A | | 9/1999 | Gueziec et al. | |
| 6,106,466 | A | * | 8/2000 | Sheehan et al. | 600/443 |

(Continued)

FOREIGN PATENT DOCUMENTS

| | | | | | |
|---|---|---|---|---|---|
| EP | 1504712 | A1 | | 2/2005 | |
| WO | 0224051 | A2 | | 3/2002 | |
| WO | WO 2007113055 | A2 | * | 10/2007 | 600/117 |
| WO | 200894949 | | | 8/2008 | |

OTHER PUBLICATIONS

Advisory Action mailed Mar. 5, 2012 for U.S. Appl. No. 12/411,515, filed Mar. 26, 2009.

(Continued)

*Primary Examiner* — John P Leubecker
*Assistant Examiner* — Ronald D Colque

(57) ABSTRACT

Landmark directional guidance is provided to an operator of an endoscopic device by displaying graphical representations of vectors adjacent a current image captured by an image capturing device disposed at a tip of the endoscopic device and being displayed at the time on a display screen, wherein the graphical representations of the vectors point in directions that the endoscope tip is to be steered in order to move towards associated landmarks such as anatomic structures in a patient.

18 Claims, 8 Drawing Sheets

112
141
111
100
114
110
120
130
POSITION PROCESSOR
116
140
IMAGE PROCESSOR
155
150
115
MEMORY
DISPLAY PROCESSOR
600
160
PRIMARY SCREEN
AUXILIARY SCREEN

(56) References Cited

U.S. PATENT DOCUMENTS 6,246,898 B1 6/2001 Vesely et al.
6,256,090 B1 7/2001 Chen et al.
6,295,368 B1 9/2001 Hasegawa et al.
6,346,940 B1 2/2002 Fukunaga
6,468,265 B1 10/2002 Evans et al.
6,522,906 B1 2/2003 Salisbury, Jr. et al.
6,580,938 B1 * 6/2003 Acker .......................... 600/424
6,747,646 B2 6/2004 Gueziec et al.
6,774,624 B2 * 8/2004 Anderson et al. ........ 324/207.17
6,869,396 B2 3/2005 Belson
6,892,090 B2 * 5/2005 Verard et al. .................. 600/424
6,923,768 B2 8/2005 Camus et al.
6,978,166 B2 * 12/2005 Foley et al. .................. 600/425
7,072,707 B2 7/2006 Galloway, Jr. et al.
7,139,601 B2 11/2006 Bucholz et al.
7,144,367 B2 12/2006 Chen et al.
7,155,315 B2 12/2006 Niemeyer et al.
7,233,820 B2 6/2007 Gilboa
7,300,398 B2 11/2007 Chefdhotel et al.
7,343,195 B2 3/2008 Strommer et al.
7,366,562 B2 * 4/2008 Dukesherer et al. .......... 600/424
7,381,183 B2 6/2008 Hale et al.
7,398,116 B2 7/2008 Edwards
7,427,263 B2 9/2008 Hoeg et al.
7,517,320 B2 4/2009 Wibowo et al.
7,542,791 B2 * 6/2009 Mire et al. .................... 600/407
7,561,733 B2 7/2009 Vilsmeier et al.
7,599,730 B2 * 10/2009 Hunter et al. ................. 600/424
7,636,595 B2 * 12/2009 Marquart et al. ............. 600/424
7,657,300 B2 * 2/2010 Hunter et al. ................. 600/424
7,660,623 B2 * 2/2010 Hunter et al. ................. 600/424
7,697,972 B2 * 4/2010 Verard et al. .................. 600/424
7,751,865 B2 * 7/2010 Jascob et al. .................. 600/424
7,756,563 B2 7/2010 Higgins et al.
7,818,044 B2 * 10/2010 Dukesherer et al. .......... 600/424
7,840,253 B2 * 11/2010 Tremblay et al. ............. 600/424
7,889,905 B2 2/2011 Higgins et al.
7,901,348 B2 3/2011 Soper et al.
7,967,742 B2 6/2011 Hoeg et al.
7,971,341 B2 * 7/2011 Dukesherer et al. ............ 29/606
8,050,523 B2 11/2011 Younge et al.
8,102,416 B2 1/2012 Ito et al.
8,180,428 B2 * 5/2012 Kaiser et al. .................. 600/411
8,239,001 B2 * 8/2012 Verard et al. .................. 600/424
8,320,991 B2 * 11/2012 Jascob et al. .................. 600/424
8,337,397 B2 12/2012 Prisco et al.
8,600,478 B2 * 12/2013 Verard et al. .................. 600/424
2001/0027272 A1 10/2001 Saito et al.
2002/0087169 A1 7/2002 Brock et al.
2002/0156363 A1 * 10/2002 Hunter et al. ................. 600/410
2003/0038802 A1 * 2/2003 Johnson et al. ............... 345/420
2003/0055317 A1 3/2003 Taniguchi et al.
2003/0055410 A1 3/2003 Evans et al.
2003/0114730 A1 6/2003 Hale et al.
2003/0220541 A1 11/2003 Salisbury, Jr. et al.
2004/0034300 A1 * 2/2004 Verard et al. .................. 600/424
2004/0097805 A1 * 5/2004 Verard et al. .................. 600/428
2004/0097806 A1 * 5/2004 Hunter et al. ................. 600/434
2004/0138548 A1 * 7/2004 Strommer et al. ............ 600/407
2004/0152970 A1 * 8/2004 Hunter et al. ................. 600/424
2004/0152972 A1 * 8/2004 Hunter .......................... 600/424
2004/0171924 A1 * 9/2004 Mire et al. .................... 600/407
2004/0199072 A1 * 10/2004 Sprouse et al. ............... 600/424
2005/0033149 A1 * 2/2005 Strommer et al. ............ 600/407
2005/0054895 A1 3/2005 Hoeg et al.
2005/0085715 A1 * 4/2005 Dukesherer et al. .......... 600/424
2005/0085718 A1 * 4/2005 Shahidi ......................... 600/424
2005/0085720 A1 * 4/2005 Jascob et al. .................. 600/424
2005/0113643 A1 5/2005 Hale et al.
2005/0143651 A1 * 6/2005 Verard et al. .................. 600/424
2005/0182295 A1 8/2005 Soper et al.
2005/0182319 A1 8/2005 Glossop
2005/0197559 A1 9/2005 Boese et al.
2006/0013523 A1 1/2006 Childlers et al.
2006/0025677 A1 * 2/2006 Verard et al. .................. 600/423
2006/0058647 A1 3/2006 Strommer et al.
2006/0084867 A1 * 4/2006 Tremblay et al. ............. 600/434
2006/0094958 A1 * 5/2006 Marquart et al. ............. 600/434
2006/0149134 A1 7/2006 Soper et al.
2006/0184016 A1 8/2006 Glossop
2006/0189842 A1 8/2006 Hoeg et al.
2006/0264740 A1 * 11/2006 Van Vaals ..................... 600/414
2006/0269275 A1 * 11/2006 Krause et al. ................. 396/310
2007/0065077 A1 3/2007 Childers et al.
2007/0066866 A1 3/2007 Noguchi et al.
2007/0066887 A1 * 3/2007 Mire et al. .................... 600/424
2007/0135803 A1 * 6/2007 Belson ............................. 606/1
2007/0156019 A1 7/2007 Larkin et al.
2007/0173694 A1 7/2007 Tsuji et al.
2007/0265503 A1 11/2007 Schlesinger et al.
2007/0270650 A1 11/2007 Eno et al.
2007/0293721 A1 12/2007 Gilboa
2008/0071142 A1 * 3/2008 Gattani et al. ................ 600/117
2008/0071143 A1 * 3/2008 Gattani et al. ................ 600/117
2008/0114238 A1 * 5/2008 Lloyd ........................... 600/436
2008/0118135 A1 5/2008 Averbuch et al.
2008/0132909 A1 * 6/2008 Jascob et al. .................. 606/130
2008/0161677 A1 7/2008 Sutherland et al.
2008/0171937 A1 * 7/2008 Dukesherer et al. .......... 600/424
2008/0172069 A1 * 7/2008 Dukesherer et al. .......... 606/130
2008/0195109 A1 * 8/2008 Hunter et al. ................... 606/87
2008/0200926 A1 * 8/2008 Verard et al. .................. 606/130
2008/0207997 A1 8/2008 Higgins et al.
2008/0212082 A1 9/2008 Froggatt et al.
2008/0214922 A1 * 9/2008 Hartmann et al. ............ 600/407
2008/0218770 A1 9/2008 Moll et al.
2008/0262297 A1 10/2008 Gilboa et al.
2008/0262312 A1 10/2008 Carroll et al.
2008/0285909 A1 11/2008 Younge et al.
2009/0030306 A1 1/2009 Miyoshi et al.
2009/0118742 A1 * 5/2009 Hartmann et al. ............ 606/130
2009/0131746 A1 * 5/2009 Seo et al. ...................... 600/101
2009/0137952 A1 5/2009 Ramamurthy et al.
2009/0161927 A1 6/2009 Mori et al.
2009/0175518 A1 * 7/2009 Ikuma et al. .................. 382/128
2009/0192524 A1 7/2009 Itkowitz et al.
2009/0234217 A1 * 9/2009 Mire et al. .................... 600/407
2009/0281417 A1 * 11/2009 Hartmann et al. ............ 600/424
2009/0324161 A1 12/2009 Prisco
2009/0326556 A1 12/2009 Diolaiti et al.
2010/0249506 A1 9/2010 Prisco
2010/0249507 A1 9/2010 Prisco et al.
2010/0305435 A1 * 12/2010 Magill .......................... 600/426
2011/0098532 A1 * 4/2011 Graumann et al. ........... 600/117
2011/0098533 A1 4/2011 Onoda et al.
2012/0046521 A1 * 2/2012 Hunter et al. ................. 600/104
2013/0231556 A1 * 9/2013 Holsing et al. ................ 600/424

OTHER PUBLICATIONS

Banovac, Filip et al., “Liver Tumor Biopsy in a Respiring Phantom with the Assistance of a Novel Electromagnetic Navigation Device,” 2002, pp. 200-207, Springer-Verlag.

Bardaro, Sergio Jose and Lee Swanstrom, “Development of advanced endoscopes for Natural Orifice Transluminal Endoscopic Surgery (NOTES),” J. Minimally Invasive Therapy, vol. 15, Issue 6, 2006, pp. 378-383.

Burschka, Darius et al., “Navigating Inner Space: 3-D Assistance for Minimally Invasive Surgery,” Robotics and Autonomous Systems, 2005, pp. 5-26, vol. 52—Issue 1, Elsevier.

Chiu, Adeline M. et al., “3-D Image Guidance for Minimally Invasive Robotic Coronary Artery Bypass,” The Heart Surgery Forum, Jun. 8, 2000, vol. 3—No. 3, pp. 224-231.

Coste-Maniere; Eve et al., “Optimal Planning of Robotically Assisted Heart Surgery: First Results on the Transfer Precision in the Operating Room,” The International Journal of Robotics Research, 2004, pp. 539-548, vol. 23—Issue 4-5, SAGE Publications.

Doignon, C. et al., “Model-based 3-D pose estimation and feature tracking for robot assisted surgery with medical imaging,” published in “From Features to Actions: Unifying Perspectives in Computational and Robot Vision” workshop at the IEEE International Conference on Robotics and Automation, Apr. 2007, 10 pages. Internet:

(56) References Cited

OTHER PUBLICATIONS http://hal.archives-ouvertes.fr/docs/00/35/06/47/PDF/2007_wkicra_doignon.pdf.

Examiner Initiated Interview Summary mailed May 9, 2012 for U.S. Appl. No. 12/411,515, filed Mar. 26, 2009.

Final Office Action mailed Jan. 9, 2012 for U.S. Appl. No. 12/411,515, filed Mar. 26, 2009.

International Search Report and Written Opinion for Application No. PCT/US2010/027660, mailed on Jun. 28, 2010, 12 pages.

Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-50, vol. 2, Springer Verlag.

Levy, L. Campbell et al., "Training for NOTES," J. Gastrointestinal Endoscopy Clinics of North America, vol. 18, 2008, pp. 343-360.

Non-Final Office Action mailed Mar. 7, 2012 for U.S. Appl. No. 12/411,501, filed Mar. 26, 2009.

Non-Final Office Action mailed Oct. 11, 2012 for U.S. Appl. No. 12/411,501, filed Mar. 26, 2009.

Non-Final Office Action mailed Jul. 26, 2011 for U.S. Appl. No. 12/411,515, filed Mar. 26, 2009.

PCT/US10/27760 International Search Report and Written Opinion of the International Searching Authority, mailed Jun. 28, 2010, 14 pages.

Pearl, Jonathan P. and Jeffrey L. Ponsky, "Natural orifice transluminal endoscopic surgery: Past, present and future," Editorial in J. Minimal Access Surgery, vol. 3, Issue 2, Apr.-Jun. 2007, pp. 43-46.

Proceedings of Medicine Meets Virtual Reality II: Interactive Technology & Healthcare: Visionary Applications for Simulation Visualization Robotics, 1994, Elsevier, 275 Total Pages.

Rao, G.V. et al., "NOTES: Human Experience," J. Gastrointestinal Endoscopy Clinics of North America, vol. 18, 2008, pp. 361-370.

Swanstrom, Lee and Bin Zheng, "Spatial Orientation and Off-Axis Challenges for NOTES," J. Gastrointestinal Endoscopy Clinics of North America, vol. 18, 2008, pp. 315-324.

Szeliski, Richard and Heung-Yeung Shum, "Creating full view panoramic image mosaics and environment maps," Proceedings of the 24th annual conference on Computer graphics and interactive techniques (SIGGRAPH '97), Aug. 3-8, 1997, Los Angeles, California, published by ACM, pp. 251-258.

Szeliski, Richard, "Image Alignment and Stitching: A Tutorial," Preliminary Draft dated Jan. 26, 2005, Microsoft Technical Report MSR-TR-2004-92, 71 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

METHOD AND SYSTEM FOR PROVIDING VISUAL GUIDANCE TO AN OPERATOR FOR STEERING A TIP OF AN ENDOSCOPIC DEVICE TOWARD ONE OR MORE LANDMARKS IN A PATIENT

CROSS REFERNCE TO RELATED APPLICATIONS

This application is a continuation patent application of U.S. patent application Ser. No. 12/411,515, filed Mar. 26, 2009and entitled "METHOD AND SYSTEMS FOR PROVIDING VISUAL GUIDANCE TO AN OPERATOR FOR STEERING A TIP OF AN ENDOSCOPIC DEVICE TOWARD ONE OR MORE LANDMARKS IN A PATIENT, " which is incorporated by reference herein, in its entirety.

FIELD OF THE INVENTION

The present invention generally relates to endoscopic devices and in particular, to a method and system for providing visual guidance to an operator for steering a tip of an endoscopic device towards one or more landmarks in a patient.

BACKGROUND OF THE INVENTION

Minimally invasive surgical procedures are known to offer many benefits over traditional open surgery techniques, including less pain, shorter hospital stays, quicker return to normal activities, minimal scarring, reduced recovery time, and less injury to tissue. To perform such procedures, entry into the patient may be made through an incision or a natural body orifice. Both robotic and manually operated minimally invasive surgical devices may be used.

One example of a minimally invasive surgical robotic system is the da Vinci® Surgical System from Intuitive Surgical, Inc., of Sunnyvale, Calif. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device at a surgical site. Each of the medical devices may be inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

An endoscope is a medical device that allows physicians to capture images of and diagnose problems with internal body organs by inserting the device either through a natural orifice or a surgeon created opening and guiding it to a target site within a patient. In some cases, it may also be used to perform medical procedures on the internal body organs. It may be steerable so that its distal tip is controllably oriented for navigation purposes. An image capturing device such as a stereoscopic or monoscopic camera may be provided at its distal tip so that images captured by the camera from that perspective may be viewed on a display screen by the surgeon. To perform various medical procedures at the target site, surgical tools, such as those used for cutting, grasping, cauterizing, etc., may extend out of the endoscope's distal tip.

The endoscope may be rigid such as those used in laparoscopy or it may be flexible so that it is capable of following the curvatures of body lumens. It may also be rigidizable and/or robotic. A rigidizable endoscope is an endoscope that has at least one section of its flexible body that can be made substantially rigid by a mechanical locking mechanism. A robotic endoscope is a flexible endoscope that has at least one section that bends under a computer controlled servo mechanism. It may also be a capsule like the EndoCapsule by Olympus or a tethered capsule in which case it is not controllably oriented for navigation purposes and gets moved in the patient anatomy by gravity, forces applied by the anatomy or by other surgical devices.

Natural Orifice Transluminal Endoscopic Surgery ("NOTES") may employ a steerable endoscope to perform surgical procedures on patients. As an example, a flexible endoscope may be guided through one of the body's orifices and enter the abdomen from the inside of the patient, rather than through a minimally invasive incision from the outside. For example, in "transgastric" surgery, instruments are passed through the mouth and into the stomach. A gastrotomy is then performed so that the instruments may enter the abdomen and be used by the surgeon to perform a medical procedure within the abdominal cavity. Once the procedure is completed, the instruments are withdrawn along with any tissue removed during the procedure, and the entry point is closed back up. Because no incisions are made in the patient to accommodate entry of the endoscope, NOTES may be even less painful than surgery using minimally invasive incisions. Also, since it uses a natural body orifice instead of incisions to enter the body, it may result in reduced needs for general anesthetics and faster recovery times.

During the operation of a steerable endoscope, such as in a NOTES application, the endoscope tip may be turned multiple times and in different directions while moving towards a target site. As a consequence, the flexible endoscope may wind up looping around itself and disorienting the operator so as to make it difficult for the operator to keep track of the current direction of the endoscope tip if its captured image fails to clearly indicate its current direction with respect to the target site. In contrast, the operator may have a relatively rigid connection to the view in conventional laparoscopy.

If the operator accidentally moves the endoscope tip in the wrong direction, the tip may inadvertently perforate or otherwise damage tissue causing harm to the patient. Even if such harm is avoided by carefully moving the endoscope tip, additional time is required to repeatedly ascertain the true direction of the endoscope relative to the target site in the patient. Thus, the time required to perform the procedure is lengthened which adds to the cost of the surgery and increases health safety concerns.

OBJECTS AND SUMMARY OF THE INVENTION

Accordingly, one object of one or more aspects of the present invention is a method, and a system for performing the method, of providing visual guidance to an operator for steering an endoscopic device towards one or more landmarks in a patient.

This and additional objects are accomplished by the various aspects of the present invention, wherein briefly stated, one aspect is a computer implemented method for providing guidance to steer an endoscopic device towards one or more landmarks in a patient, the method comprising: determining a current position of a reference point on the endoscopic device relative to a reference frame; determining a first vector from the current position of the reference point to a position of a first landmark relative to the reference frame; transforming the first vector from the reference frame to an image reference frame that corresponds to the perspective of an image capturing device disposed at a tip of the endoscopic device; and displaying a graphical representation of the transformed first vector along with a current image captured by the image capturing device on a display screen so as to indicate a direction to steer the tip of the endoscopic device towards the first landmark.

Another aspect is a system comprising: a display screen; an endoscopic device; and one or more processors adapted to determine a current position of a reference point on the endoscopic device relative to a reference frame, determine a first vector from the current position of the reference point to a position of a first landmark relative to the reference frame, transform the first vector from the reference frame to an image reference frame that corresponds to the perspective of an image capturing device disposed at a tip of the endoscopic device, and display a graphical representation of the transformed first vector along with a current image captured by the image capturing device on a display screen so as to indicate a direction to steer the tip of the endoscopic device towards the first landmark.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
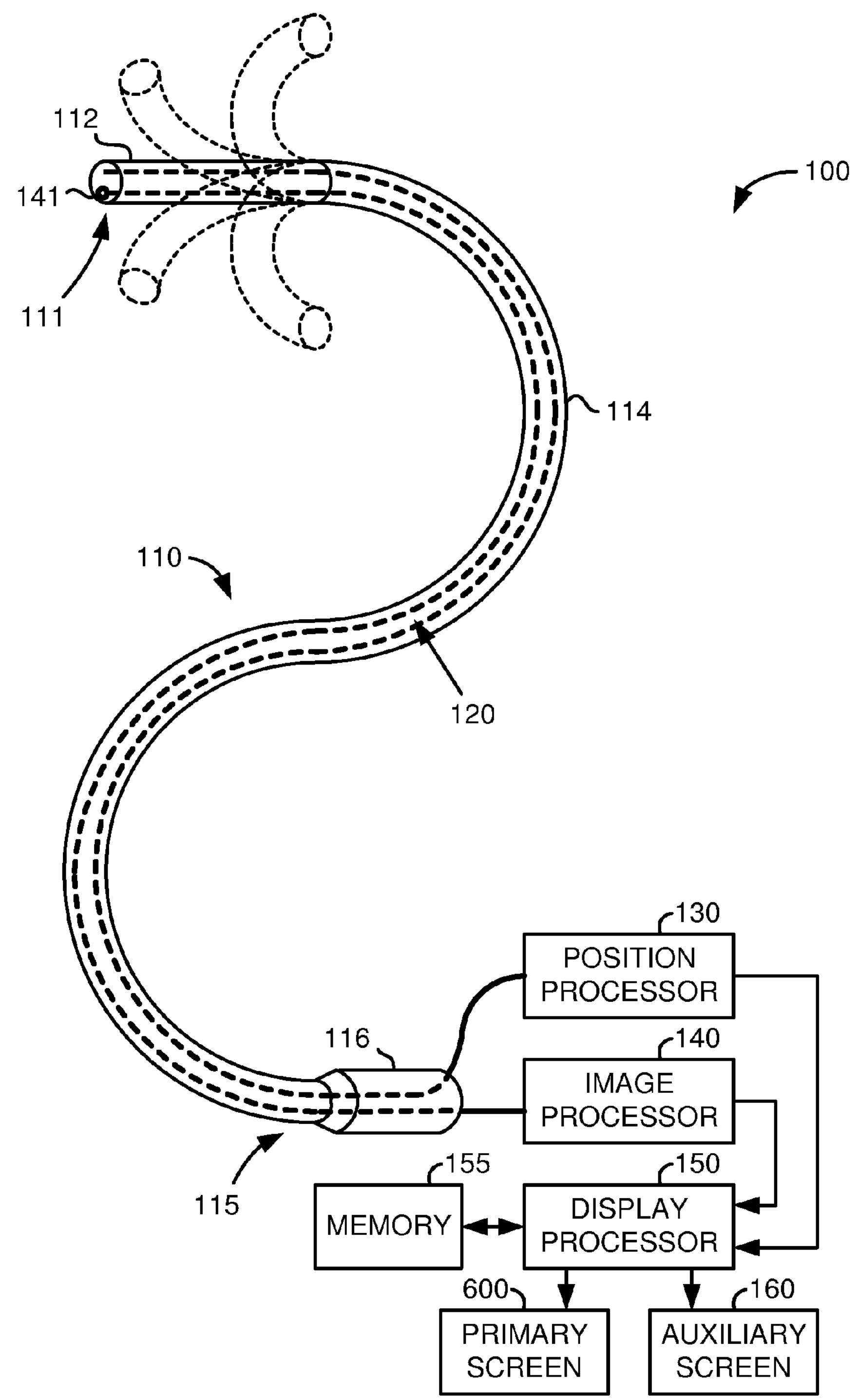
FIG. 1 illustrates a steerable endoscope system utilizing aspects of the present invention.

FIG. 1 illustrates, as an example, a system 100 including a steerable endoscope 110, one or more fiber optic cables 120 inserted in the endoscope 110, a position processor 130, an image processor 140, an image capturing device 141, a display processor 150, a primary display screen 600, and an auxiliary display screen 160. Although shown as separate units, the position processor 130, image processor 140 and display processor 150 may each be implemented as hardware, firmware, software or a combination thereof, which interact with or are otherwise executed by one or more computers, such as the one or more computers 200 depicted in FIG. 2. The primary and auxiliary display screens, 600 and 160, are preferably computer monitors capable of displaying three-dimensional images to an operator of the system 100. However, for cost considerations, either or both of the primary and auxiliary display screens, 600 and 160, may be a standard computer monitor capable of only displaying two-dimensional images.

The endoscope 110, in this example, has a flexible body 114, a steerable tip 112 at its distal end 111 and a handle or electromechanical interface 116 at its proximal end 115. Control cables (not shown) or other control means typically extend from the handle or electromechanical interface 116 to the steerable tip 112 so that the tip 112 may be controllably bent or turned as shown for example by dotted line versions of the bent tip 112. Although a steerable endoscope is described in this example, the present invention is not to be limited to endoscopes of this type and may be practiced with other endoscopic devices (such as rigid, rigidizable, robotic, or capsule endoscopes) as well.

A stereoscopic or monoscopic camera 141 is provided at the distal end 111 for capturing images that are transmitted to and processed by the image processor 140 and/or display processor 150 and displayed on the primary display screen 600 and/or auxiliary display screen 160 according to the various aspects of the invention as described herein. One of a plurality of fiber optic cables 120 may be coupled at its proximal end to a light source (not shown) for illumination purposes at the distal end 111. Others of the fiber optic cables 120 may be configured with bend or shape sensors such as Fiber Bragg Gratings (or other strain sensors such as those employing Rayleigh scattering) so that light passing through the fiber optic cable is processed by the position processor 130 to determine a current position and shape of the endoscope 110 including the orientation of its distal tip 112. In addition to the fiber optic cables 120 extending through the endoscope 110, one or more additional fiber optic cables (not shown) configured with strain sensors may be attached to the endoscope 110 so as to provide position information of the endoscope 110 at the attachment point.

When the steerable endoscope 110 is manipulated manually by an operator, a handle 116 is used with appropriate levers or other control mechanism(s) for controllably orienting the endoscope tip 112 by pulling appropriate cables (not shown) which couple such control mechanisms of the handle 116 to the tip 112. On the other hand, when the steerable endoscope 110 is manipulated teleoperatively by an operator, an electromechanical interface 116 is used instead of a handle.

Figure 3:
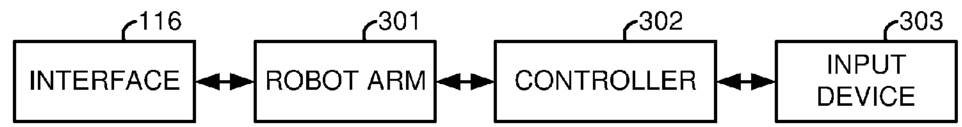
FIG. 3 illustrates a block diagram of a teleoperative portion of a steerable endoscope system utilizing aspects of the present invention.

As shown in FIG. 3, the electromechanical interface 116 allows the endoscope 110 to be electrically and mechanically coupled to a robot arm 301 whose movement is controlled by a controller 302 in response to operator manipulation of an input device 303. Either or both the interface 116 and the robot arm 301 include motors that drive the cables used to steer the endoscope tip 112. In addition to controlling bending of the endoscope's tip 112, the robot arm 301 may also be configured to insert/retract the endoscope 110 into and out of an aperture (e.g., natural orifice or minimally invasive incision) in the patient, rotate the endoscope 110 about its central axis, and/or rotate the electromechanical interface 116 about a pivot point at the aperture. The controller 302 is preferably implemented as hardware, firmware or software (or a combination thereof) in the one or more computers 200 along with the processors 130, 140, 150.

Details on the determination of the endoscope's position and bending using Fiber Bragg Gratings may be found, for examples, in U.S. 2007/0156019 A1 entitled "Robotic Surgery System Including Position Sensors Using Fiber Bragg Gratings", U.S. 2008/0212082 A1 entitled "Fiber Optic Position and/or Shape Sensing Based on Rayleigh Scatter", U.S. 2008/0218770 A1 entitled "Robotic Surgical Instrument and Methods using Bragg Fiber Sensors", and U.S. application Ser. No. 12/164,829 entitled "Fiber Optic Shape Sensor, each of which is incorporated herein by reference. Details on a conventional steerable endoscope may be found for example in U.S. Pat. No. 6,869,396 B2 entitled "Steerable Endoscope and Improved Method of Insertion".

Figure 4:
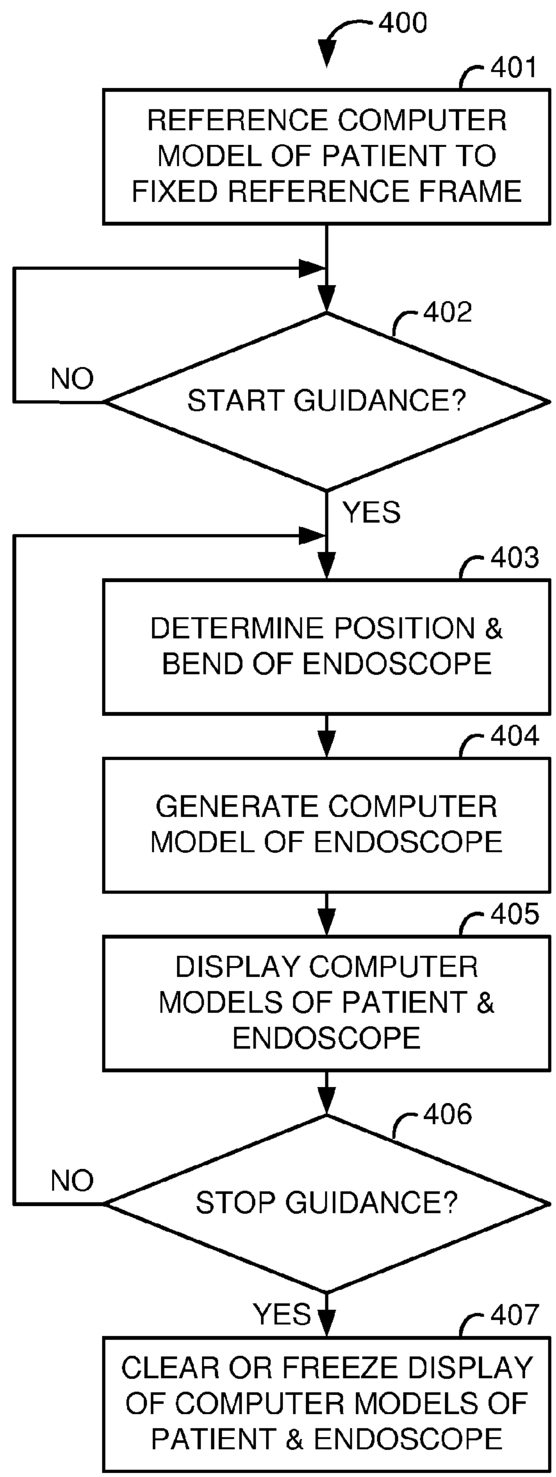
FIG. 4 illustrates a flow diagram of a computer implemented method for assisting an operator in endoscopic navigation, utilizing aspects of the present invention.

FIG. 4 illustrates, as an example, a flow diagram of a computer implemented method 400 for assisting an operator in endoscopic navigation of the steerable endoscope 110 towards a site in a patient. The computer in this case is preferably the one or more computers 200 that include the processors 130, 140, 150.

In 401, a patient computer model stored in memory 155 is referenced to a fixed reference frame (i.e., one that does not move during the medical procedure to be performed using the endoscope 110) by first referencing points on a live patient who is generally prone on an operating table with the fixed reference frame, then associating the referenced points with corresponding points on the patient computer model.

For example, using a pointer device whose tip position may be readily determined in the fixed reference frame (such as the endoscope's tip 112), the operator may move the pointer device so that it first touches the mouth of the patient to establish a first reference point corresponding to the mouth of the patient computer model. The operator may then move the pointer device so that it next touches the right and left crest of the iliac of the patient to establish a second reference point corresponding to the right and left crest of the iliac of the patient computer model. Other points such as the navel and the left and right arm pits may also be used to establish more reference points. By referencing the patient computer model to the patient in this manner, the proper size (i.e., length and width) of the patient computer model may also be established as well as its alignment with the patient and its position in the fixed reference frame. Thus, with just a few points, the patient computer model may be properly scaled and aligned (i.e., conformed) with the patient using model information in an anthropometry database in the memory 155.

Figure 7:
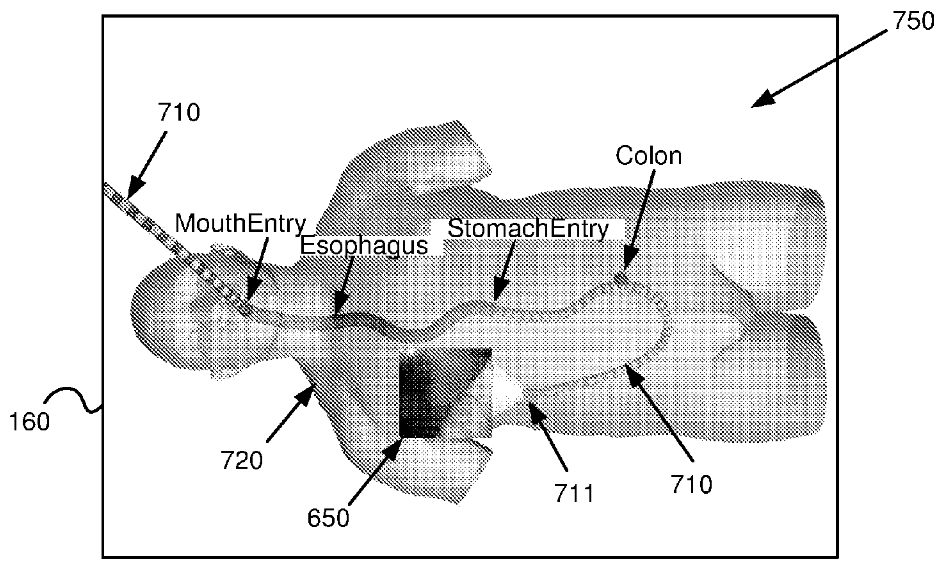
FIG. 7 illustrates an auxiliary display screen displaying an anterior-posterior view of registered patient and endoscopic device models as generated by a system utilizing aspects of the present invention.
Figure 8:
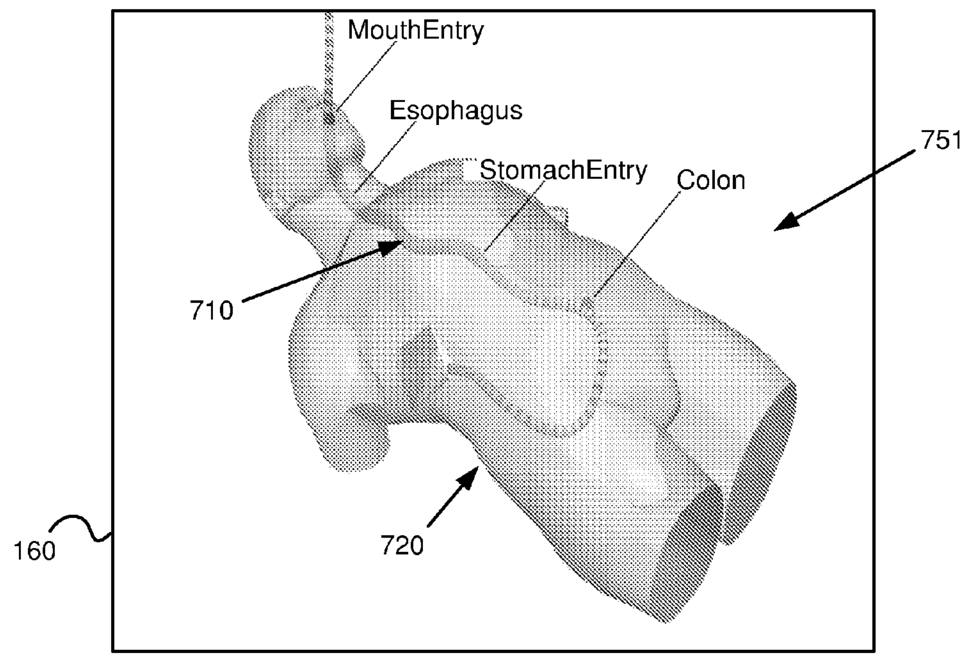
FIG. 8 illustrates an auxiliary display screen displaying an oblique view of patient and endoscopic device models as generated by a system utilizing aspects of the present invention.
Figure 9:
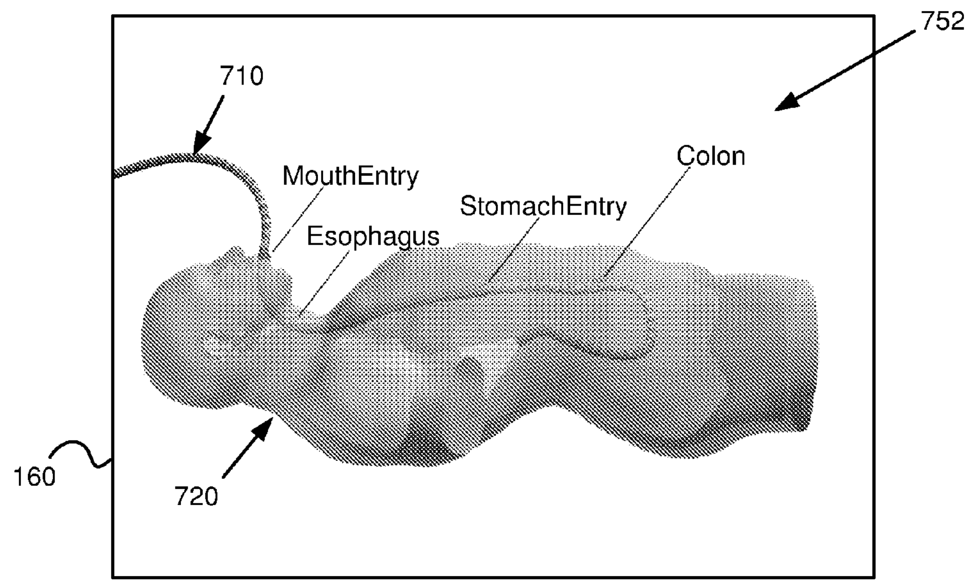
FIG. 9 illustrates an auxiliary display screen displaying a lateral-medial view of patient and endoscopic device models as generated by a system utilizing aspects of the present invention.

Several patient computer models may be stored in memory 155. For example, a number of generic patient computer models may be stored so that a different model may be used depending on the age, sex, size, etc., of the patient. Preferably, each of the models is a three-dimensional computer model including at least a head and torso (such as seen in FIGS. 7-9) so that all natural orifices are included as well as potential target sites for performing diagnostic or surgical procedures on a patient. Three-dimensional computer models of the actual patient may also be stored and used with the present system if available, such as may be generated using a Computed Tomography (CT) scan. Alternatively, the surgeon or assistant may move the distal tip 112 over the surface of the patient's body to map its profile and provide sufficient information to the position processor 130 to generate information for a three-dimensional computer model of the patient which it stores in the memory 155.

In 402, a determination is made whether or not the operator has issued a start guidance command. The operator may issue the start guidance command in any one of a number of ways such as depressing an input button or flipping a switch on the input device 303 when the steerable endoscope 110 is being controlled teleoperatively, or depressing an input button or flipping a switch on the handle 116 when the steerable endoscope 110 is being controlled manually. Other ways may include voice actuation using a microphone and voice recognition processor (not shown) that may be implemented in or operatively coupled to the one or more computers 200; a foot pedal (not shown) that may be depressed by the operator so as to turn on or off the guidance; and a graphical user interface using the auxiliary display screen 160, the primary display screen 600 or another display screen (not shown) that the operator may interact with using an input device.

If the determination in 402 is NO (i.e., navigation guidance mode has not been initiated by the operator), then the method loops through 402 each process cycle (or other programmed cycle) until a YES determination is made, at which time, the method proceeds to 403.

In 403, the current position and shape (e.g., bending) of the endoscope 110 is determined by the position processor 130 using information received from one or more optical fibers configured with shape sensors that has been inserted in the flexible body 114 of the endoscope 110. As an example of one such optical fiber, referring to FIG. 5, the distal end of an optical fiber 501 extends to the endoscope's tip 112 and its proximal end is attached to a base point 502 whose position in the fixed reference frame is known or readily determinable by the position processor 130. Preferably, the position processor 130 is also attached or otherwise coupled to the base point 502 so that the processor 130 may receive information from the bend sensors of the optical fiber 501 at that point.

Since the length of the fiber optic cable 501 is known, its proximal end is fixed to a known location, and its distal end extends out to the endoscope's tip 112, the current position and orientation of the tip 112 in the fixed reference frame may be readily determined from the current bending of the optical fiber 501 as indicated by information received from the bend sensors. Although only one fiber optic cable 501 is shown for illustrative purposes, multiple fibers or a single fiber with multiple cores configured with strain sensors are preferably employed for determining the shape of the endoscope body 114 and distal tip 112, such as described using shape sensors in previously incorporated by reference U.S. 2007/0156019 A1, U.S. 2008/0212082 A1, and U.S. application Ser. No. 12/164,829.

In 404, a computer model that is indicative of the current configuration of the flexible endoscope 110 is generated using a model of the endoscope stored in the memory 155 and modifying it to reflect the shape information received from the optical fibers configured as shape sensors. Preferably, both the stored and generated computer models of the endoscope 110 are three-dimensional models.

In 405, the patient computer model generated in 401 and the endoscope computer model generated in 404 are displayed together properly registered with respect to each other according to their respective positions in the fixed reference frame on the auxiliary display screen 160. Thus, the operator of the steerable endoscope 110 is provided a view of the current shape of the endoscope 110 relative to the patient's body in order to provide guidance to the operator for navigating the endoscope 110 to a target site within the patient. A visual indication of the target site may also be displayed as well as computer models or other indications of any anatomic structures or body lumens that the endoscope 110 may encounter or pass through in its path to the target site.

The manner in which the patient and endoscope computer models are displayed on the auxiliary display screen 160 is preferably selectable by the operator using any one or more of a number of well known techniques such as clickable icons and pull down menus provided on the auxiliary display screen 160 and/or primary display screen 600. For example, icons may be provided on the auxiliary display screen 160 so that the operator may select an anterior-posterior view 750, oblique view 751, or lateral-medial view 752 of the patient and endoscope 110, such as shown respectively in FIGS. 7, 8 and 9, by clicking on the appropriate icon using a computer mouse or other suitable device.

Figure 6:
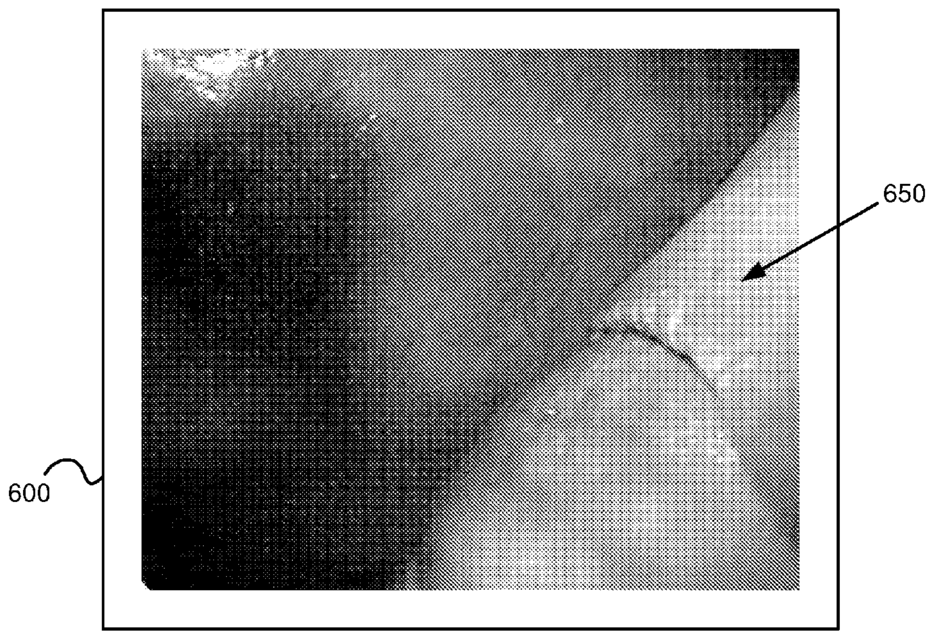
FIG. 6 illustrates a primary display screen displaying an image captured by a steerable endoscope as viewed in a system utilizing aspects of the present invention.

Referring to FIG. 7, the anterior-posterior view 750 of the patient computer model 720 and endoscope computer model 710 is shown along with indications of various landmarks along the endoscope's path (e.g., mouth entry, esophagus, stomach entry, and colon) on the auxiliary display screen 160. In addition, real-time images captured by the endoscope 110 (such as the captured image 650 shown in FIG. 6 being displayed on a primary display screen 600) may also be displayed on the auxiliary display screen 160 adjacent to (or appearing to emanate from) the distal end 711 of the endoscope computer model 710.

Figure 10:
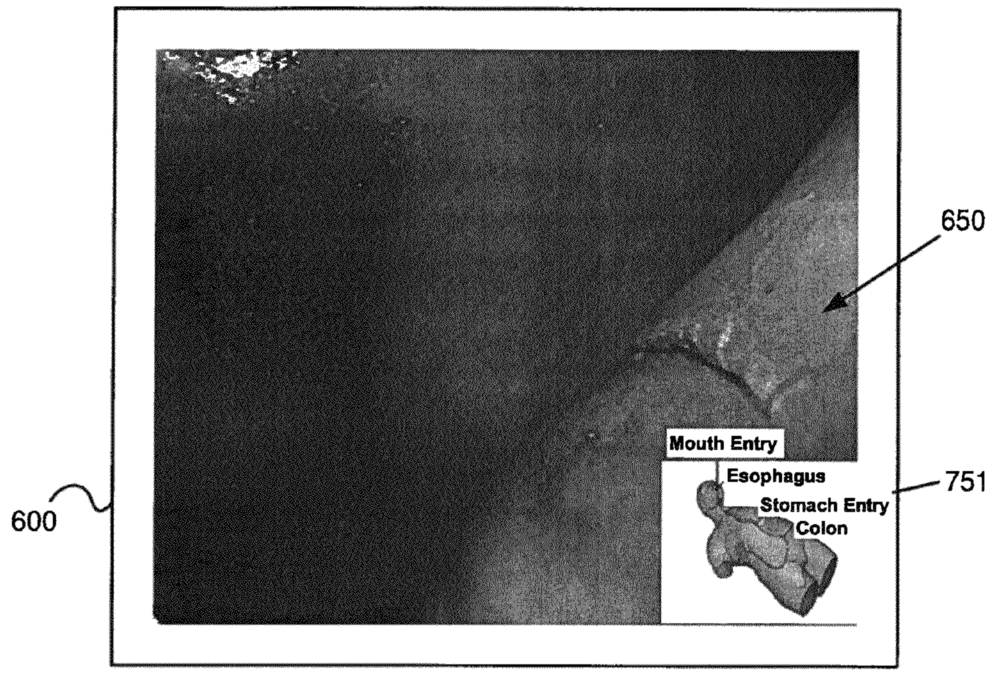
FIG. 10 illustrates a primary display screen displaying an image captured by an endoscopic device in a main window area and an oblique view of patient and endoscopic device models in a picture-in-picture window area as generated by a system utilizing aspects of the present invention.
Figure 11:
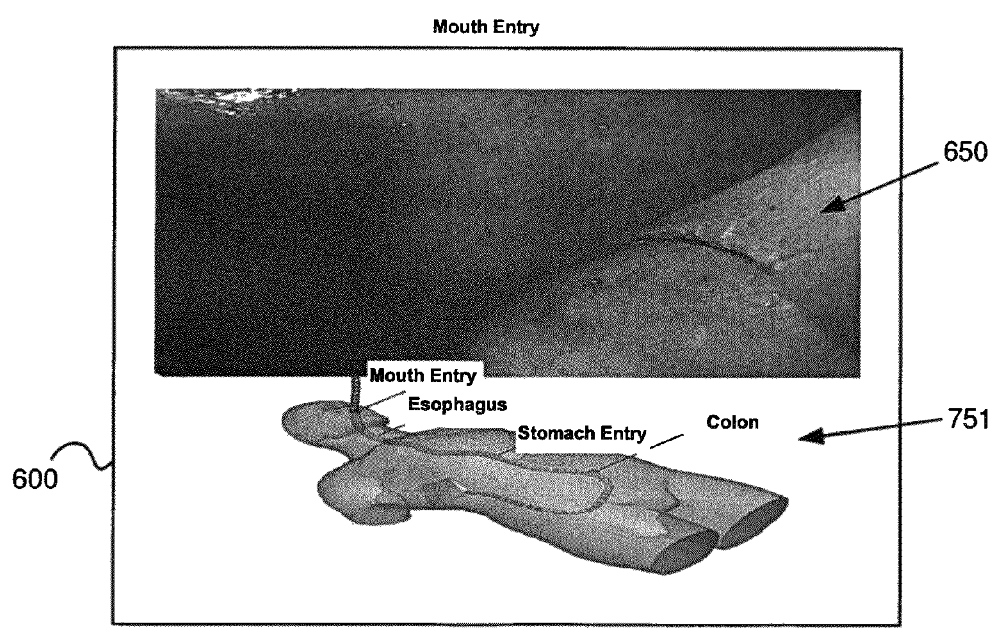
FIG. 11 illustrates a primary display screen displaying an image captured by an endoscopic device in a first area and an oblique view of patient and endoscopic device models in a second area as generated by a system utilizing aspects of the present invention.

In addition to (or alternative of) displaying the patient and endoscope computer models, 720 and 710, on the auxiliary display screen 160, the computer models may be displayed on the primary display screen 600 along with the captured image 650. For example, the oblique view 751 may be shown as a picture-in-picture insert to the captured image 650 on the primary display screen 600 as shown in FIG. 10 or it may be shown in an adjacent window to that of the captured image 650 on the primary display screen 600 as shown in FIG. 11.

Referring back to FIG. 4, in 406, a determination is made whether or not the operator has issued a stop guidance command. The operator may issue the stop guidance command in any one of a number of ways similar to, but complementary of those in which the operator issues the start guidance command.

If the determination in 406 is NO (i.e., navigation guidance mode has not been stopped by the operator), then the method loops back to 403 to update the current position and bend of the endoscope 110 and display a computer model of it along with the computer model of the patient for the next process cycle (or other programmed cycle). On the other hand, if the determination in 406 is YES (i.e., navigation guidance mode has been stopped by the operator), then the method proceeds to 407 in which the display processor 150 either causes the computer models of the patient and endoscope to no longer be displayed on the auxiliary display screen 160 and/or primary display screen 600 or freezes them on the display screen.

During the whole endoscopic procedure, starting from the insertion of the endoscope 110 in the patient's body, the proposed method and invention stores in the memory device 155 digital versions of images periodically captured by the camera 141 (at the distal tip 112 of the endoscope 110) together with the three-dimensional (3-D) position and orientation information of the camera 141 (as determined by the position processor 130) with respect to the patient anatomy at the times (e.g., at a processing rate of 30 HZ) that the images were captured. Timestamps indicating the times are also stored in the memory device 155. The resulting database provides endoscopic images tagged by their respective 3-D locations in the fixed reference frame that can be accessed at any successive time by the display processor 150 for the purpose of computing synthetic two-dimensional (2-D) and three-dimensional (3-D) views of the visited anatomy. Thus, a full recording of the endoscopic procedure may be stored in the memory device 155 (preferably a mass storage device, such as a hard drive, for this application) that may be played back on the display screens 600 and 160 for educational and/or archival purposes.

A first synthetic 2-D view can be computed by assembling (stitching together) multiple endoscopic images taken from neighboring 3-D locations into a single larger panoramic image according to the well known Computer Vision technique known as mosaicking (see for instance the seminal work by R. Szeliski, H. Y. Shum, Creating full view panoramic image mosaics and environment maps, In *Proc. of ACM SIGGRAPH,* 1997.) Endoscopic panoramas allow improved endoscopic navigation by providing a larger field of view then the endoscopic camera is capable of hence delivering greater awareness of the surrounding anatomy to the surgeon. Thus, the captured images shown in various figures herein on the primary display screen 600 are preferably panoramic images generated by the display processor 150 by mosaicking images retrieved from the memory device 155 which are representative of the most recently captured images by the camera 141.

As an additional endoscopic navigation tool, graphical indications showing steering directions to previously defined landmarks in the patient are also provided as an aspect of the present invention.

Figure 12:
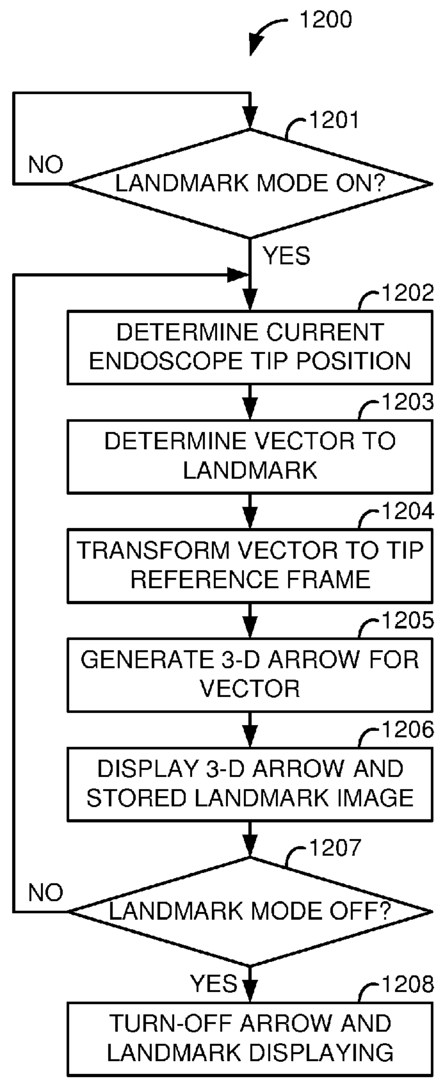
FIG. 12 illustrates a flow diagram of a computer implemented method of providing directional guidance to maneuver an endoscopic device to one or more landmarks, utilizing aspects of the present invention.

FIG. 12 illustrates, as an example, a flow diagram of a computer implemented method 1200 for providing directional guidance to maneuver the steerable endoscope 110 to one or more landmarks in a patient. The computer in this case is preferably the one or more computers 200 that include the processors 130, 140, 150.

Figure 2:
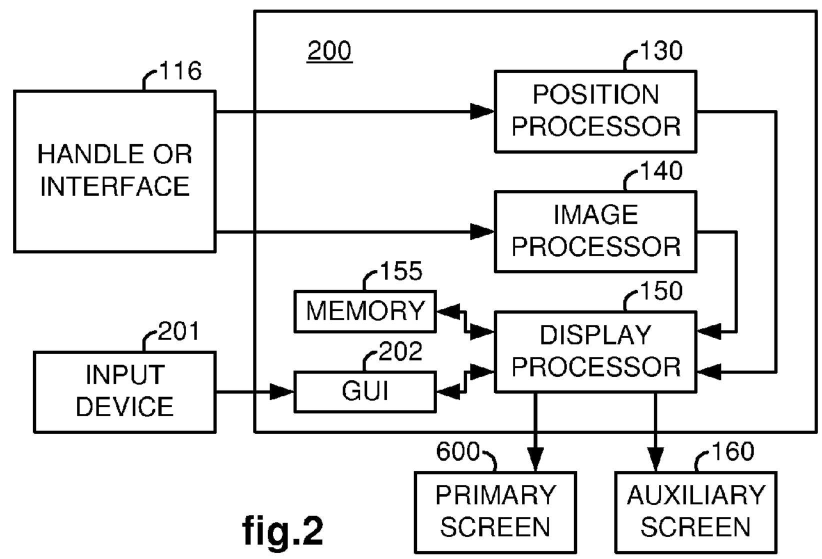
FIG. 2 illustrates a block diagram of a processing portion of a steerable endoscope system utilizing aspects of the present invention.

In 1201, a determination is made whether or not the operator has turned on a landmarks directional guidance mode. The operator may turn on and/or off this mode in any one of a number of ways such as depressing an input button or flipping a switch on the input device 303 when the steerable endoscope 110 is being controlled teleoperatively, or depressing an input button or flipping a switch on the handle 116 when the steerable endoscope 110 is being controlled manually. Other ways may include voice actuation using a microphone and voice recognition processor (not shown) that may be implemented in or operatively coupled to the one or more computers 200; a foot pedal (not shown) that may be depressed by the operator so as to turn on or off the mode; and a graphical user interface (GUI) 202 using the display screen 600 that the operator may interact with using an input device 201 as shown in FIG. 2 to turn on and off the mode as well as specify other aspects or parameters of the method as described herein.

If the determination in 1201 is NO (i.e., landmark directional guidance is turned off), then the method loops through 1201 each process cycle (or other programmed cycle) until a YES determination is made, at which time, the method proceeds to 1202.

In 1202, the current position of the endoscope tip 112 in a fixed reference frame (i.e., a reference frame that does not move during the performance of a medical procedure using the endoscope 110) is determined by the position processor 130 using information received from the optical fibers configured with strain sensors (e.g., optical fiber 501 in FIG. 5) that have been inserted in the flexible body 114 of the endoscope 110.

Figure 5:
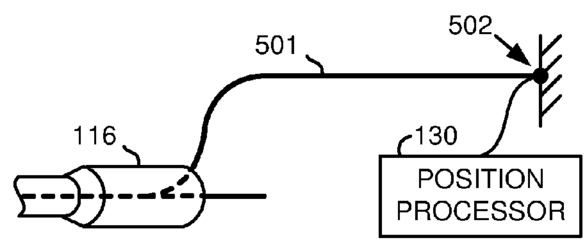
FIG. 5 illustrates parts of a position determining portion of a steerable endoscope system utilizing aspects of the present invention.

The current position and orientation of the endoscope tip 112 may be readily determined in the fixed reference frame (for example, as previously explained in reference to 403 of FIG. 4) from the current bending of the optical fibers as indicated by information received from their strain sensors since their lengths are known, their proximal ends are fixed to a known location (such as fiber 501 to base point 502 as shown in FIG. 5), and their distal ends extend to the endoscope's tip 112.

In 1203, a vector connecting the current position of the endoscope tip 112 to the position of each landmark to which guidance indications are to be provided is determined by the display processor 150 using the endoscope tip position determined in 1202 and landmark positions stored in the memory device 155.

Typically, the landmarks are established by the operator as he or she guides the steerable endoscope 110 along its path from an entry point to a target site in the patient. As an example, FIG. 14 shows an oblique view of a patient's head and torso where the steerable endoscope 110 has entered through the patient's mouth and its tip 112 guided to a target site. In this example, the endoscope 110 has been guided through the esophagus to the patient's stomach. The stomach was then entered and the endoscope 110 guided to the target site. Along the way, landmarks are established at the mouth entry and stomach entry using a method such as described below in reference to FIG. 13.

Alternatively, the positions of landmarks within the patient may be based upon preoperative measured data such as generated by Computer Axial Tomography (CAT), Magnetic Resonance Imaging (MRI), or X-rays. In this case, the patient's body (as he or she is lying down on the operating room table) is referenced to the fixed reference frame and the landmarks are registered with the patient's body so that their positions are determinable in the fixed reference frame by their respective positions in the patient's body. The landmark positions are then stored in the memory device 155 (or other storage device accessible to the display processor 150). Although establishing landmarks in this manner may be time consuming and expensive, it allows the method described herein to provide directional guidance to landmarks in front of the endoscope tip 112 (i.e., between the current position of the endoscope tip and the target site), not just behind it (i.e., between the entry point into the patient and the current position of the endoscope tip).

In 1204, the vectors determined in 1203 are then transformed from the fixed reference frame to a reference frame associated with the endoscope tip 112 (or camera 141) by the display processor 150.

In 1205, 3-D arrows (or other graphical representations) indicative of the transformed vectors determined in 1204 are generated by the display processor 150. The directions of the 3-D arrows are referenced to the endoscope tip's reference frame so that they correspond to directions that the operator should steer the endoscope's tip 112 using the handle or electromechanical interface 116 as previously described.

The sizes of the 3-D arrows, on the other hand, may be generated so as to be proportional to the magnitudes of the translated vectors so that landmarks further away are represented by larger arrows. As an alternative, the sizes may be generated so as to be inversely proportional to the magnitudes of the translated vectors so that landmarks further away are represented by smaller arrows. As yet another alternative, the sizes may be generated so as to each have the same length (such as shown by arrows 1511, 1512 and 1513 in FIG. 15).

The 3-D arrows may also be color-coded so that the color of each arrow is uniquely associated with a particular anatomic structure. For example, referring to FIG. 15, a 3-D arrow 1511 indicating a steering direction towards the mouth entry landmark may be colored red, a 3-D arrow 1512 indicating a steering direction towards the stomach entry landmark may be colored yellow, and 3-D arrow 1513 indicating a steering direction towards the colon entry landmark may be colored blue. Alternatively, the edges of the display screen 600 may be colored to correspond to landmarks. The color schemes used herein may be operator defined or correspond to the color scheme used on MR viewers.

In 1206, the 3-D arrows (or other graphical representations) generated in 1205 and a current image (as currently captured at the endoscope tip 112 and processed by the image processor 140 or a panoramic image as previously described using mosaicking of the current and previously captured images) are displayed on the primary display screen 600 by the display processor 150. In addition, previously captured images of the landmarks may also be selectively or automatically retrieved from the memory device 155 and displayed adjacent or otherwise proximate to their respective 3-D arrows. The positions of the 3-D arrows may be displayed on the display screen 600 so as to relate to the orientations of the translated vectors so that, for example, arrows pointing to the left are positioned on the left side of the image and arrows pointing to the right are positioned on the right side of the image. Alternatively, the 3-D arrows may all be positioned near the same side of the image or spaced around the image. In the case where edges of the display screen 600 may be colored to correspond to landmarks, the 3-D arrow corresponding to each landmark is displayed adjacent its respective colored edge so that the association of the 3-D arrow and landmark is clear.

In addition to showing the landmarks as 3-D arrows on or near the current endoscope image on the primary display screen 600, the landmarks can be displayed together with the 3-D patient and endoscope computer models being displayed on the auxiliary display screen 160 wherein positions of stored landmarks may be shown in their proper locations relative to the patient computer model. The landmarks may be indicated, for example, by a text label with the landmark name, a thumbnail image with the stored endoscope image captured with the landmark, a small graphic icon related to the type of landmark, or with an approximate 3-D model of the landmark.

Selection of which, if any, landmark images are to be displayed may be made by the operator, for example, using the input device 201 and GUI 202 to select one display option from a menu including: all landmark images to be displayed, no landmark images displayed, and only nearest landmark image to be displayed. Alternatively, the operator may not be provided an option and the choice pre-selected and programmed into the display processor 150. Position, size, color and other options for displaying the 3-D arrows on the display screen 600 may be selected by the operator using the input device 201 and GUI 202 as shown in FIG. 2.

Figure 15:
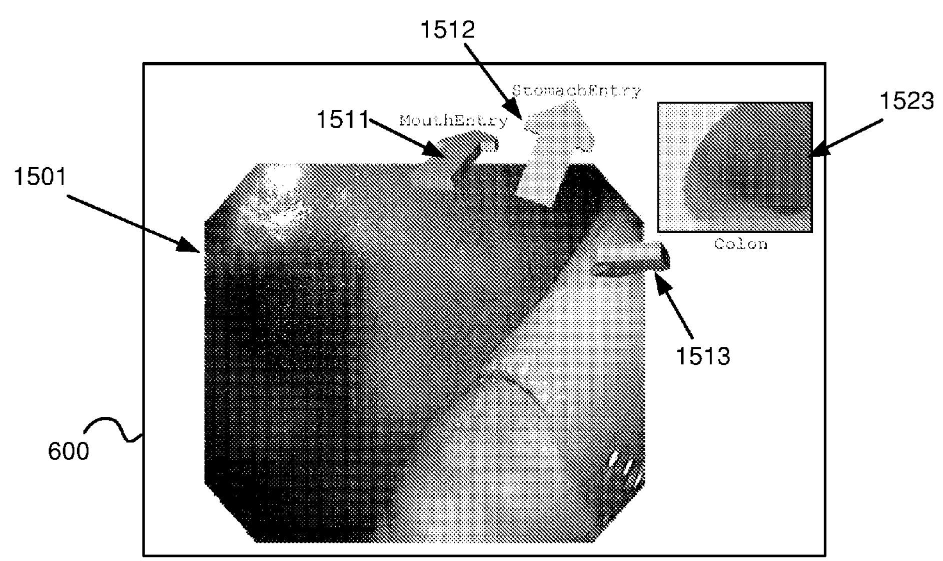
FIG. 15 illustrates a primary display screen displaying a current image captured by an endoscopic device and graphical representations of various vectors indicating directions to corresponding landmarks along with an image associated with one of the landmarks, according to a method utilizing aspects of the present invention.

As an example of such displaying, FIG. 15 shows the display screen 600 having a current image 1501 (i.e., an image currently captured by the endoscope 110 or a panoramic image as described elsewhere herein) displayed on it along with arrows 1511, 1512 and 1513 respectively providing directional guidance to the mouth entry, stomach entry and colon entry landmarks. In addition, a previously captured image 1523 of the colon entry landmark is shown being displayed in a window adjacent to its associated arrow 1513, which happens to be the nearest landmark to the current position of the endoscope tip 112.

In 1207, a determination is made whether or not the operator has turned off the landmark directional guidance mode. The operator may turn off the mode in any one of a number of ways similar to, but in an opposite manner of those in which the operator turned on the landmark guidance mode (e.g., placing a switch in an "off" vs. "on" position).

If the determination in 1207 is NO (i.e., landmark directional guidance mode has not been turned off by the operator), then the method loops back to 1202 to update the landmark directional vectors (e.g., 1511, 1512, 1513 in FIG. 15) as the endoscope tip 112 is being guided to the target site and display updated graphical representations of the translated vectors on the display screen 600 along with a current image captured by the endoscope 110. On the other hand, if the determination in 1207 is YES (i.e., landmark direction guidance mode has been turned off by the operator), then the method proceeds to 1208 in which the display processor 150 causes the graphical representations of the translated vectors and any corresponding landmark captured images to no longer be displayed on the display screen 600.

It is to be appreciated that even though landmark directional guidance mode may be turned off, the operator may still be guiding the steerable endoscope 110 towards the target site and continually updated images captured at the endoscope tip 112 (and processed by image processor 130) may still be displayed on the display screen 600 by the display processor 150. For example, referring to FIG. 15, the display screen 600 may still have the current or panoramic image 1501 displayed on it, but the arrows 1511, 1512, 1513 and landmark image 1523 are no longer displayed after the operator turns off the landmark directional guidance mode.

It is also to be appreciated that the operator may interactively establish landmarks for which directional guidance is to be provided at any time while guiding the steerable endoscope 110 towards the target site. In particular, landmark establishment may be performed while landmark directional guidance mode is turned on as well as off.

Figure 13:
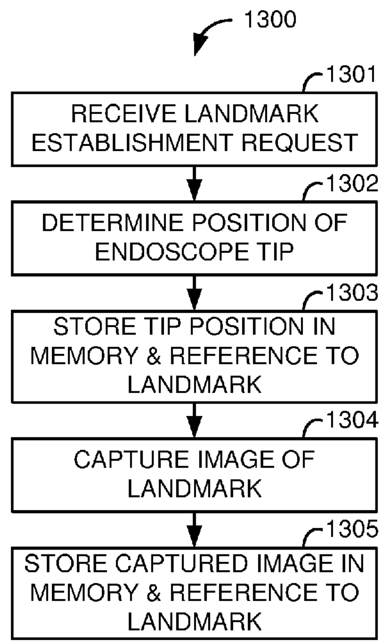
FIG. 13 illustrates a flow diagram of a computer implemented method for establishing landmarks using an endoscopic device as it moves by the landmarks, utilizing aspects of the present invention.
Figure 14:
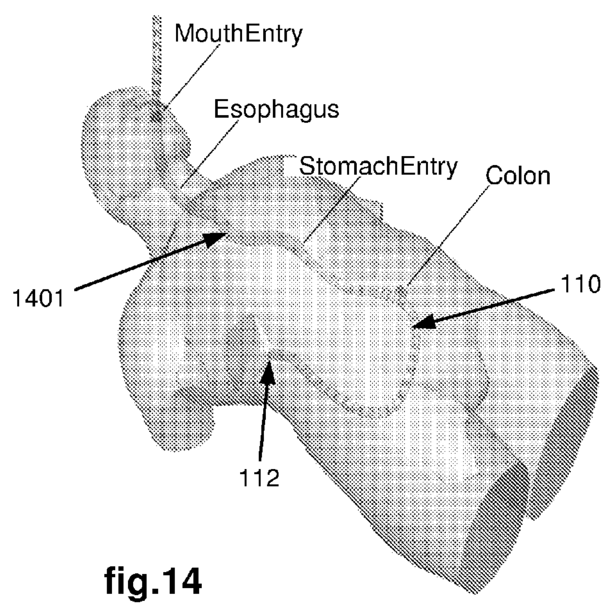
FIG. 14 illustrates an oblique view of a patient torso with an endoscopic device inserted therein and examples of various landmarks as employed in a system utilizing aspects of the present invention.

FIG. 13 illustrates, as an example, a computer implemented method 1300 for establishing anatomic structure landmarks as the steerable endoscope 110 is being guided through a patient's body. As in the case of the method 1200 described in reference to FIG. 12, the computer in this case is preferably the one or more computers 200 that include the processors 130, 140, 150. In particular, it is preferably performed by the display processor 150 concurrently with other activities performed by the display processor 150 as described herein.

In 1301, a landmark establishment request is received from the operator. The operator may initiate the request in any one of various well known interactive techniques including those previously described in reference to turning on and off the landmark directional guidance mode (but preferably a different one so as not confuse the two actions).

In 1302, the current position of the endoscope tip 112 in the fixed reference frame is determined. Note that if the landmark directional guidance mode is turned on, this action is the same as 1202 of method 1200 and therefore, it does not have to be performed since the result from 1202 may be used in this case (i.e., it does not have to be performed a second time or twice in the same process cycle).

In 1303, the current position of the endoscope tip 112 is then stored in the memory device 155 and referenced as the position of the landmark whose establishment has been requested. In 1304, a current image captured at the endoscope tip 112 is identified as an image of the landmark and in 1305, information of the image is also stored in the memory device 155 and referenced as the image of the landmark whose establishment has been requested.

As may be appreciated in performing the method 1300, the order in which actions 1302 and 1304 occur is not important. In fact, the image processor 140 may process captured images at a different rate than that in which the position processor 130 determines current positions of the endoscope tip 112. Therefore, the two actions may differ in the time as well as in the order in which they may each occur. In any event, upon receiving the landmark establishment request in 1301, the next determined position of the endoscope tip 112 is stored in the memory device 155 and the next captured image received from the image processor 130 is stored in the memory device 155 without concern about which one occurs first.

In addition to the establishment of landmarks while navigating the endoscope 110 towards a target site within the patient, anatomic structures (such as the esophagus, stomach, colon, etc.) may be measured using position information of the endoscope tip 112 as it moves from one end of the anatomic structure to the other. Information of the measured anatomic structure may than be used to align and size 3-D models or preoperative measured data of the anatomic structures to their proper positions inside the patient's body and display the structures together with the 3-D patient computer model on the auxiliary display screen 160. As an example, FIG. 14 shows how the measured positions of the mouth and stomach entry landmarks have been used, together with the intermediate shape of the endoscope, to align and size a 3-D model of the esophagus connecting the mouth to the stomach entry. The esophagus model is then displayable as a 3-D curved tube 1401, together with the 3-D models of the patient and the endoscope 110 on the auxiliary display screen 160.

Although the various aspects of the present invention have been described with respect to one or more preferred embodiments, it will be understood that the invention is entitled to full protection within the full scope of the appended claims.

What is claimed is:

1. A method for navigating a steerable instrument in a patient anatomy, the method comprising:

receiving a first landmark establishment request;

responsive to receiving the request, recording information about a reference portion of the steerable instrument located at a first anatomic landmark in the patient anatomy;

referencing the recorded information as first landmark information;

registering the first landmark information to a model of the patient anatomy; and providing guidance for navigating the steerable instrument along a path through a plurality of anatomic landmarks, including the first anatomic landmark, to a target location within the patient anatomy.

2. The method of claim 1 wherein the first landmark information includes position information.

3. The method of claim 1 wherein the first landmark information includes an image from the reference portion of the steerable instrument captured by an image capture device.

4. The method of claim 1 wherein the first landmark information includes shape information.

5. The method of claim 1 wherein the first landmark information includes a timestamp .

6. The method of claim 1 wherein the first landmark information includes a graphical representation.

7. The method of claim 6 further comprising displaying the model of the patient anatomy registered with the graphical representation.

8. The method of claim 1 wherein the guidance includes a model of the path between the plurality of anatomic landmarks.

9. The method of claim 8 further comprising displaying the model of the path registered with the model of the patient anatomy.

10. A method for navigating a steerable instrument in a patient anatomy, the method comprising:

recording first information about a reference portion of the steerable instrument located at a first anatomic landmark in the patient anatomy;

referencing the recorded first information as first landmark information, the recorded first information including position information for the reference portion located at the first anatomic landmark and including an image captured by the steerable instrument while the reference portion is located at the first anatomic location;

recording second information about the reference portion of the steerable instrument located at a second anatomic landmark in the patient anatomy;

referencing the recorded second information as second landmark information, the recorded second information including position information for the reference portion located at the second anatomic landmark and including an image captured by the steerable instrument while the reference portion is located at the second anatomic location; and providing guidance for navigating a guided instrument along a path through the first and second anatomic landmarks.

11. The method of claim 10 wherein the position information of the first and second landmark information is recorded with respect to a fixed reference frame.

12. The method of claim 10 further comprising registering the first and second landmark information to a model of the patient anatomy.

13. The method of claim 12 further comprising displaying the model of the patient anatomy registered with graphical representations of the first and second landmark information.

14. The method of claim 12 wherein the guidance includes a model of the path between the first and second anatomic landmarks.

15. The method of claim 14 further comprising displaying the model of the path registered with the model of the patient anatomy.

16. The method of claim 10 wherein the steerable instrument includes an image capture device.

17. The method of claim 10 wherein the guided instrument is the steerable instrument.

18. The method of claim 10 wherein the first and second landmark information each include at least one of: information about a shape of the steerable instrument; a timestamp, and a graphical representation.

* * * * *